US009265653B2

(12) United States Patent  
Chen et al.

(10) Patent No.: US 9,265,653 B2
(45) Date of Patent: Feb. 23, 2016

(54) THERMAL THERAPY DEVICE INCORPORATING CARBON NANOTUBES

(75) Inventors: Lu-Zhuo Chen, Beijing (CN); Chang-Hong Liu, Beijing (CN); Shou-Shan Fan, Beijing (CN)

(73) Assignees: Tsinghua University, Beijing (CN); HON HAI PRECISION INDUSTRY CO., LTD., New Taipei (TW)

( * ) Notice: Subject to any disclaimer, the term of this patent is extended or adjusted under 35 U.S.C. 154(b) by 514 days.

(21) Appl. No.: 13/109,200

(22) Filed: May 17, 2011

(65) Prior Publication Data

US 2012/0172953 A1    Jul. 5, 2012

(30) Foreign Application Priority Data

Dec. 31, 2010    (CN) .......................... 2010 1 0618082

(51) Int. Cl.
*A61F 7/00*    (2006.01)
*B82Y 30/00*   (2011.01)
*A61H 7/00*    (2006.01)

(52) U.S. Cl.
CPC ................ *A61F 7/007* (2013.01); *B82Y 30/00* (2013.01); *A61F 2007/0071* (2013.01); *A61H 7/007* (2013.01); *A61H 2201/0207* (2013.01)

(58) Field of Classification Search
USPC ....................................... 607/96–114; 5/421
See application file for complete search history.

(56) References Cited

U.S. PATENT DOCUMENTS

| 7,045,108 | B2 | 5/2006 | Jiang et al. | |
| 7,704,480 | B2 | 4/2010 | Jiang et al. | |
| 2008/0248235 | A1 | 10/2008 | Feng et al. | |
| 2008/0299031 | A1 | 12/2008 | Liu et al. | |
| 2010/0122980 | A1* | 5/2010 | Wang et al. | 219/553 |
| 2010/0243637 | A1* | 9/2010 | Liu et al. | 219/520 |
| 2011/0094217 | A1* | 4/2011 | Chen et al. | 60/528 |

FOREIGN PATENT DOCUMENTS

| CN | 101848564 | 9/2010 |
| WO | WO2007015710 | 2/2007 |

* cited by examiner

*Primary Examiner* — Joseph Stoklosa
*Assistant Examiner* — Adam Avigan
(74) *Attorney, Agent, or Firm* — Novak Druce Connolly Bove + Quigg LLP

(57) ABSTRACT

A thermal therapy device includes a substrate and at least one heating unit arranged on the substrate. The at least one heating unit includes a heating element, a first electrode, and a second electrode. The heating element includes a carbon nanotube film structure and a polymer matrix. The carbon nanotube film structure is substantially parallel to and offset from a central plane of the polymer matrix. The first electrode and the second electrode are electrically connected to the carbon nanotube film structure, and control the amount of heat and deformation produced by the carbon nanotube film structure.

20 Claims, 15 Drawing Sheets

THERMAL THERAPY DEVICE INCORPORATING CARBON NANOTUBES

RELATED APPLICATIONS

This application claims all benefits accruing under 35 U.S.C. §119 from China Patent Application No. 201010618082.8, filed on Dec. 31, 2010 in the China Intellectual Property Office, hereby incorporated by reference.

BACKGROUND

1. Technical Field

The present disclosure relates to thermal therapy devices, and particularly, to a thermal therapy device incorporating carbon nanotubes for warming the body to enhance healing or improve comfort.

2. Description of Related Art

Historically, heat has been a natural remedy. It aids circulation, relieves pain, and enhances the recovery process. By increasing the temperature of the skin surface and underlying tissues, heat stimulates the thermoreceptors which then help block transmissions of pain signals to the brain, thereby increasing comfort. Heat therapy increases circulation, which helps to decrease stiffness, relaxes sore muscles, and provides soothing comfort. Many thermotherapy techniques and instrument use hot water and hot air as heating mediums generated by paraffin wax or a therapeutic lamp. Those instruments are unsatisfactory for humans for therapeutic use.

BRIEF DESCRIPTION OF THE DRAWINGS

Many aspects of the embodiments can be better understood with references to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
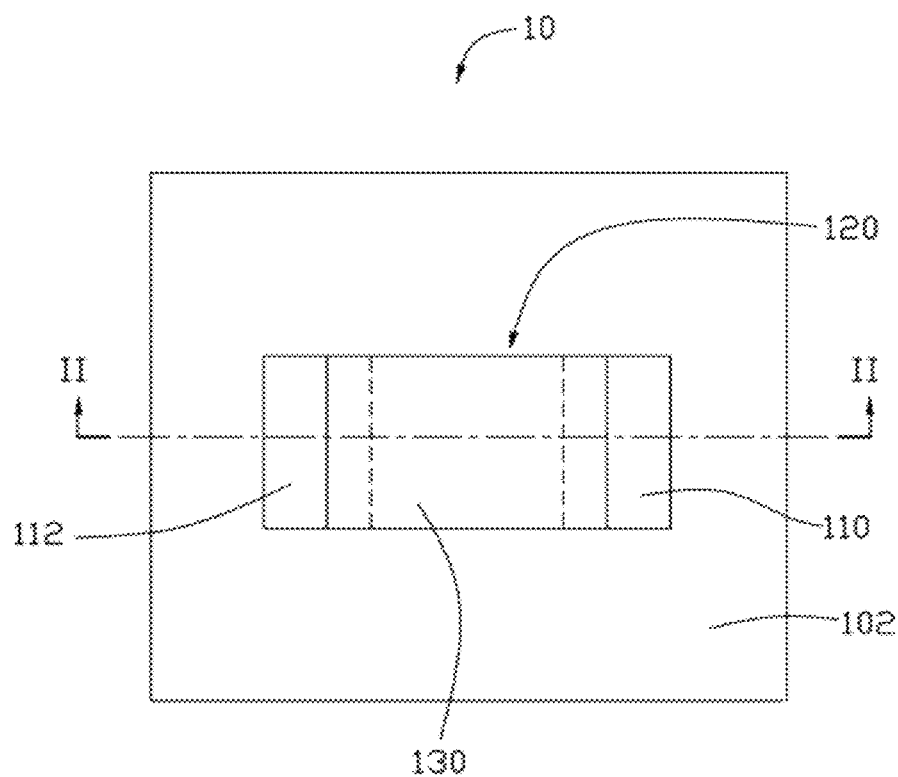
FIG. 1 is a top view of a first embodiment of a thermal therapy device.
Figure 2:
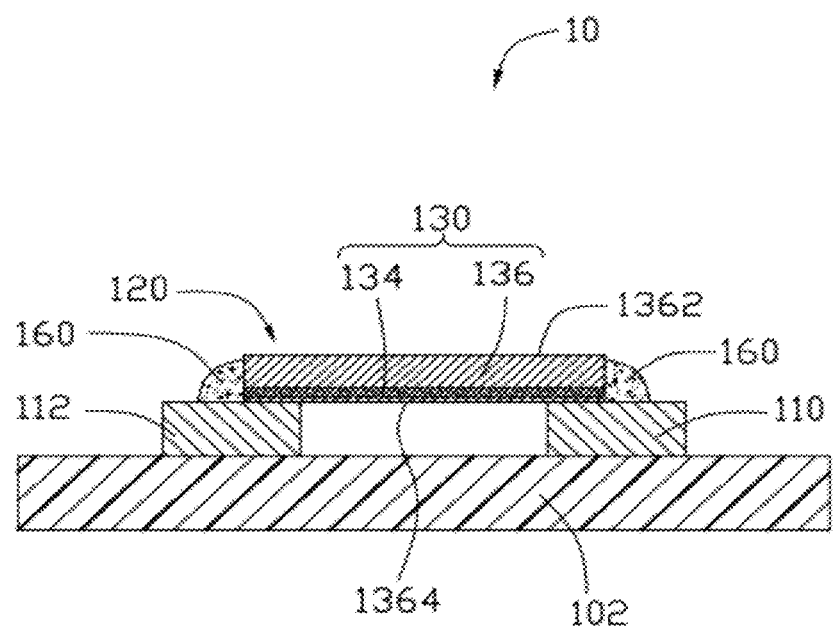
FIG. 2 is a cross-sectional view of the thermal therapy device of FIG. 1, taken along a line II-II.

Referring to FIG. 1 and FIG. 2, a first embodiment of a thermal therapy device 10 includes a substrate 102 and a heating unit 120. The heating unit 120 is installed on the substrate 102.

The substrate 102 can be made of rigid or flexible insulating materials. If the substrate 102 is made of rigid insulating materials, the substrate 102 can be made of at least one of ceramics, glass, resin, quartz, and plastic. The substrate 102 can be designed to have a shape of a tube, ball, or cuboid. The substrate 102 can be designed to have other shapes according to the contours of the portion of the body which needs thermal therapy. For example, the substrate 102 can be designed to have a tubular shape with a C-shaped cross section, to receive knee joints therein.

If the substrate 102 is made of flexible insulating materials, the substrate 102 can be made of at least one of resin, rubber, plastic, and flexible fiber. The substrate 102 made of flexible insulating materials can be bent into a desired shape, to be properly attached to the portion of the body which needs thermal therapy, to obtain a better therapeutic effect. The size and thickness of the substrate 102 is not limited, and can be designed according to the actual application. In one embodiment, the substrate 102 is a flat square rubber film with a thickness of about 5 millimeters and a side length of about 10 centimeters.

The heating unit 120 includes a first electrode 110, a second electrode 112, and a heating element 130. The first electrode 110 and the second electrode 112 are carried by the substrate 102 and are spaced from each other. The heating element 130 is electrically connected with both of the first electrode 110 and the second electrode 112.

The first electrode 110 and the second electrode 112 can be made of metal conductive materials, conductive rubber, or other materials with a conductive layer coated thereon. The first electrode 110 and the second electrode 112 can be planar conductors. The sizes of the first electrode 110 and the second electrode 112 can be designed according to the size of the heating element 130. In one embodiment, the first electrode 110 and the second electrode 112 each are a planar conductor made of metal wires which can be attached to a surface of the substrate 102 with adhesive such as polymer binder. The first electrode 110 and the second electrode 112 each have a length ranging from about 20 micrometers to about 1.5 centimeters, a width ranging from about 30 micrometers to about 1 centimeter, and a thickness ranging from about 0.4 millimeters to about 0.5 centimeters.

The heating element 130 has opposite ends. One end of the heating element 130 is installed on a surface of the first electrode 110, and the opposite end of the heating element 130 is installed on a surface of the second electrode 112. The opposite ends of the heating element 130 can be attached to top surfaces of the first electrode 110 and the second electrode 112 via a conductive adhesive 160, as a result, the heating element 130 is suspended above the substrate 102.

Figure 3:
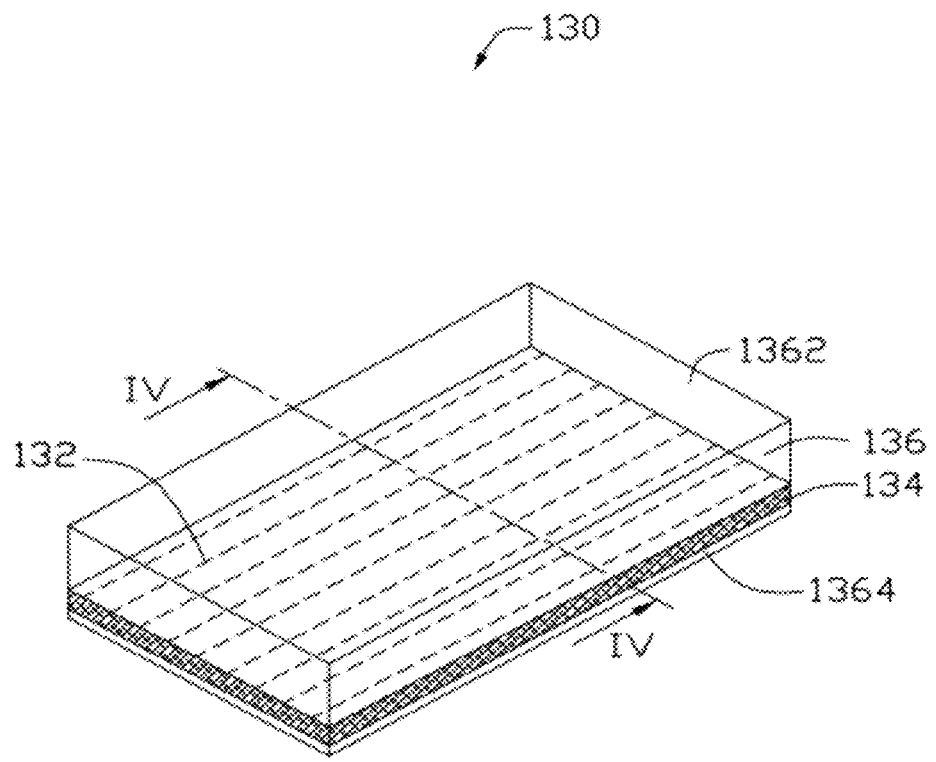
FIG. 3 is an isometric view of a heating element of FIG. 2.

As shown in FIG. 3, the heating element 130 can be a planar thin film structure. The size of the heating element 130 is not limited, and can be designed according to actual applications. In one embodiment, the heating element 130 has a length of about 1 centimeter, a width of about 0.5 centimeters, and a thickness of about 2 millimeters.

The heating element 130 includes a carbon nanotube film structure 134 and a polymer matrix 136. The carbon nanotube film structure 134 can be buried in the polymer matrix 136 to form an integral structure. The ratio between the thickness of the carbon nanotube film structure 134 and the polymer matrix 136 can be between about 1:300 to about 1:2. In one embodiment, the ratio between the thickness of the carbon nanotube film structure 134 and the polymer matrix 136 is about 1:20.

The polymer matrix 136 has a first surface 1362 and an opposite second surface 1364. The second surface 1364 is adjacent to the substrate 102. The carbon nanotube film structure 134 is disposed in the polymer matrix 136 and is adjacent to the second surface 1364 of the polymer matrix 136. The carbon nanotube film structure 134 is substantially parallel to the second surface 1364. The distance from the carbon nanotube film structure 134 to the second surface 1364 is smaller than the distance from the carbon nanotube film structure 134 to the first surface 1362. In one embodiment, the distance from the carbon nanotube film structure 134 to the second surface 1364 is about 10 micrometers to about 1 millimeter.

As described above, the carbon nanotube film structure 134 and the polymer matrix 136 together form an unsymmetrical structure when viewed along the thickness of the heating element 130. The thickness of the heating element 130 is substantially parallel to the substrate 102 towards the heating element 130. Thus, there is sufficient distance between the first surface 1362 and the carbon nanotube film structure 134 to avoid leakage of electricity which may hurt a person using the thermal therapy device 10.

Further, opposite ends of the carbon nanotube film structure 134 can extend outside of the polymer matrix 136 to electrically connect the first electrode 110 and the second electrode 112 in a one-to-one manner. Moreover, the carbon nanotube film structure 134 can also be directly attached to the second surface 1364.

Figure 4:
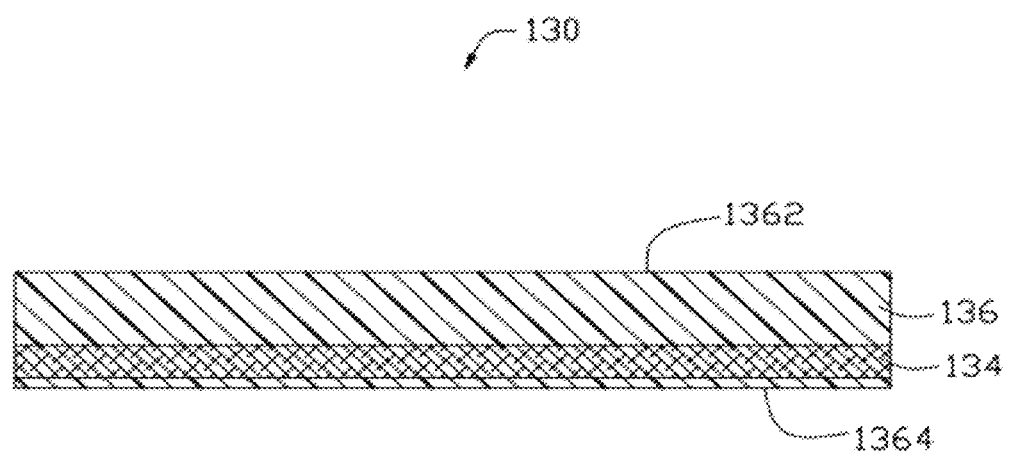
FIG. 4 is a cross-sectional view of the heating element of FIG. 3, taken along a line IV-IV.

As shown in FIG. 4, the polymer matrix 136 can be a sheet. The shape of the polymer matrix 136 is not limited and may be, for example, round or rectangular, and have other thickness ranges. A material of the polymer matrix 136 can be made of flexible materials, such as silicone elastomer, poly methyl methacrylate, polyurethane, epoxy resin, polypropylene acid ethyl ester, acrylic acid ester, polystyrene, polybutadiene, polyacrylonitrile, polyaniline, polypyrrole, polythiophene, or any combination thereof. In one embodiment, the polymer matrix 136 can be a rectangular plate made of silicone elastomer with a thickness of about 2 millimeters.

The carbon nanotube film structure 134 is a thin film structure with a width substantially equal to that of the polymer matrix 136.

The carbon nanotube film structure 134 can be at least partly embedded into the polymer matrix 136 through the second surface 1364 of the polymer matrix 136. The carbon nanotube film structure 134 can include a plurality of micropores. The polymer matrix 136 can permeate into the micropores of the carbon nanotube film structure 134. In some embodiments, the carbon nanotube film structure 134 and the polymer matrix 136 can be combined by: (1) putting the carbon nanotube film structure 134 on the polymer matrix 136 which is in a viscous-liquid state; and (2) solidifying the polymer matrix 136 after the polymer matrix 136 has permeated into the micropores of the carbon nanotube film structure 134. The carbon nanotube film structure 134 and the polymer matrix 136 can bind together because material of the polymer matrix 136 is permeated in the micropores of the carbon nanotube film structure 134. Alternatively, the entire carbon nanotube film structure 134 can be attached on the second surface 1364 of the polymer matrix 136. After the carbon nanotube film structure 134 has combined with the polymer matrix 136, the carbon nanotube film structure 134 can be substantially parallel to and offset from a central plane through the thickness of the polymer matrix 136.

The carbon nanotube film structure 134 can be a freestanding structure, that is, the carbon nanotube film structure 134 can be supported by itself and does not need a substrate for support. For example, if someone holds at least one section of the carbon nanotube film structure 134, the entire carbon nanotube film structure 134 can be lifted without being destroyed. The carbon nanotube film structure 134 includes a plurality of carbon nanotubes combined by van der Waals force. Once in a film structure, the carbon nanotubes can be used to form any desired structure. The thickness of the carbon nanotube film structure 134 is larger than 10 micrometers but smaller than 2 millimeters.

The carbon nanotubes in the carbon nanotube film structure 134 can be selected from single-walled, double-walled, and/or multi-walled carbon nanotubes. The diameter of the single-walled carbon nanotubes is in a range from about 0.5 nanometers to about 50 nanometers. The diameter of the double-walled carbon nanotubes is in a range from about 1 nanometer to about 50 nanometers. The diameter of the multi-walled carbon nanotubes is in a range from about 1.5 nanometers to about 50 nanometers. The carbon nanotube film structure 134 can be a layered structure or a linear structure. The heat capacity per unit area of the carbon nanotube film structure 134 can be less than $2 \times 10^{-4}$ $J/m^2*K$.

In one embodiment, the heat capacity per unit area of the carbon nanotube film structure 134 is less than or equal to $1.7 \times 10^{-6}$ $J/m^2*K$. The heating element 130 has a high heating efficiency and accuracy because the heat capacity of the carbon nanotube film structure 134 is very low, and the temperature of the heating element 130 can rise and fall quickly. The heating element 130 also has a high response heating speed because the heat capacity of the carbon nanotube film structure 134 is very low.

The carbon nanotubes in the carbon nanotube film structure 134 can be orderly or disorderly arranged. The term 'disordered carbon nanotube structure' refers to a structure wherein the carbon nanotubes are arranged along different directions, and the carbon nanotubes are randomly distributed. The number of the carbon nanotubes arranged along each different direction can be almost the same (e.g. uniformly disordered). The disordered carbon nanotube structure can be isotropic, namely the carbon nanotube film has properties identical in all directions of the carbon nanotube film. The carbon nanotubes in the disordered carbon nanotube structure can be entangled with each other.

The carbon nanotube film structure 134 including ordered carbon nanotubes is an ordered carbon nanotube structure. The term 'ordered carbon nanotube structure' refers to a structure where the carbon nanotubes are arranged in a consistently systematic manner, e.g., the carbon nanotubes are arranged approximately along a same direction from the first electrode 110 towards the second electrode 112.

The carbon nanotube film structure 134 can include at least one carbon nanotube film. The carbon nanotube film can be a drawn carbon nanotube film, a flocculated carbon nanotube film, or a pressed carbon nanotube film. The carbon nanotube film structure 134 can also be at least one linear carbon nanotube structure. The linear carbon nanotube structure can be an untwisted carbon nanotube wire, a twisted carbon nanotube wire, or combinations thereof. The carbon nanotube film structure 134 can also be a combination of the carbon nanotube film structure and the linear carbon nanotube structure. It is understood that any carbon nanotube film structure 134 described can be used with all embodiments.

Drawn Carbon Nanotube Film

In one embodiment, the carbon nanotube film structure 134 includes at least one drawn carbon nanotube film. A film can be drawn from a carbon nanotube array, to obtain a drawn carbon nanotube film. Examples of drawn carbon nanotube film are taught by U.S. Pat. No. 7,045,108 to Jiang et al., and WO 2007015710 to Zhang et al. The drawn carbon nanotube film includes a plurality of successive and oriented carbon nanotubes joined end-to-end by van der Waals attractive force therebetween. The drawn carbon nanotube film is a free-standing film.

Figure 5:
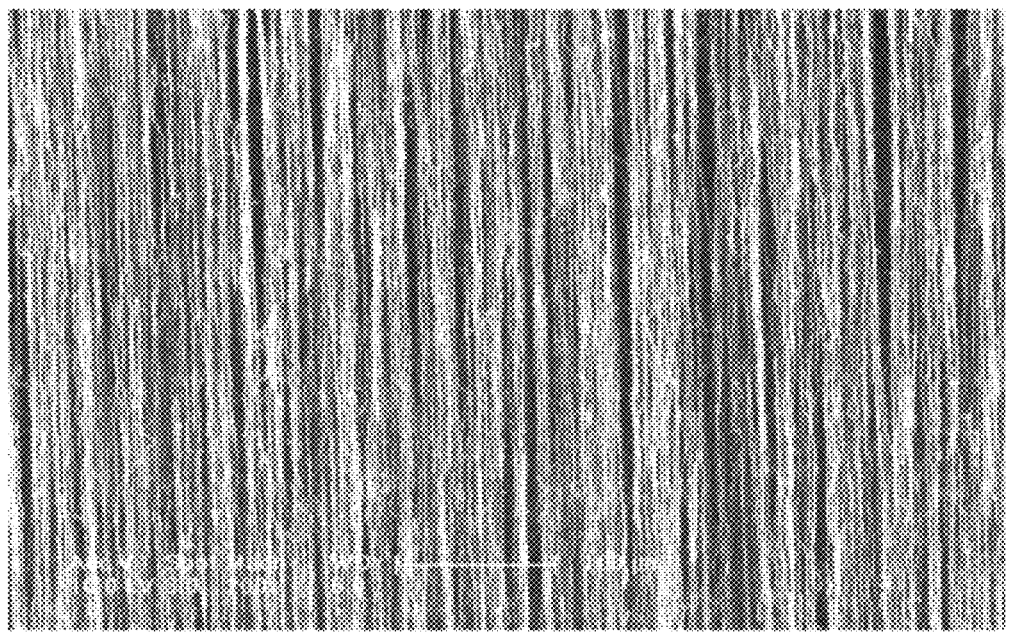
FIG. 5 is a Scanning Electron Microscope (SEM) image of a drawn carbon nanotube film.
Figure 6:
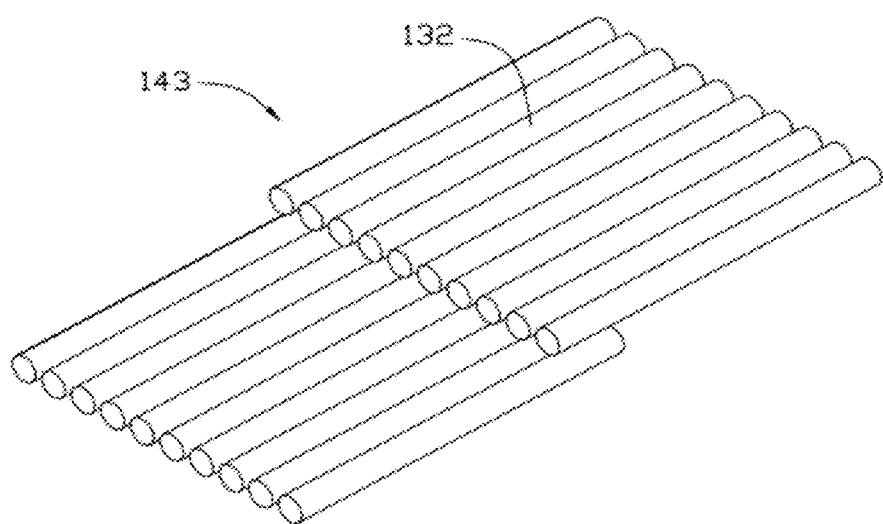
FIG. 6 is a schematic structural view of a carbon nanotube segment.

Referring to FIGS. 5 to 6, each drawn carbon nanotube film includes a plurality of successively oriented carbon nanotube segments 143 joined end-to-end by van der Waals force therebetween. Each carbon nanotube segment 143 includes a plurality of carbon nanotubes 132 substantially parallel to each other, and combined by van der Waals force therebetween.

As can be seen in FIG. 5, some variations can occur in the drawn carbon nanotube film. The carbon nanotubes 132 in the drawn carbon nanotube film are oriented along a preferred orientation. The drawn carbon nanotube film can be treated with an organic solvent to increase the mechanical strength and toughness of the drawn carbon nanotube film and reduce the coefficient of friction of the drawn carbon nanotube film. The thickness of the drawn carbon nanotube film can range from about 0.5 nm to about 100 µm.

The carbon nanotube film structure 134 can include at least two stacked drawn carbon nanotube films. In other embodiments, the carbon nanotube film structure 134 can include two or more coplanar carbon nanotube films, and can include layers of coplanar carbon nanotube films. Additionally, when the carbon nanotubes in the carbon nanotube film structure 134 are aligned along one preferred orientation (e.g., the drawn carbon nanotube film), an angle can exist between the orientations of carbon nanotubes in adjacent films, whether stacked or adjacent. Adjacent carbon nanotube films can be combined only by van der Waals force therebetween. The number of the layers of the carbon nanotube films is not limited. However, the thicker the carbon nanotube structure is, the more the specific surface area will decrease.

An angle between the aligned directions of the carbon nanotubes in two adjacent carbon nanotube films can range from about 0 degrees to about 90 degrees. If the angle between the aligned directions of the carbon nanotubes in adjacent carbon nanotube films is larger than 0 degrees, a microporous structure is defined by the carbon nanotubes in the heating element 130.

The carbon nanotube film structure 134 in an embodiment employing these films will have a plurality of micropores. The diameter of the micropores is in a range from about 1 nanometer to about 0.5 micrometers. The thickness of the drawn carbon nanotube film can be in a range form about 0.01 micrometers to about 100 micrometers.

Pressed Carbon Nanotube Film

In other embodiments, the carbon nanotube film structure 134 can include at least a pressed carbon nanotube film. The pressed carbon nanotube film can be a free-standing carbon nanotube film. The carbon nanotubes in the pressed carbon nanotube film are arranged substantially along a same direction or along different directions. The carbon nanotubes in the pressed carbon nanotube film can rest upon each other. Adjacent carbon nanotubes are attracted to each other and are combined by van der Waals force. An angle between a primary alignment direction of the carbon nanotubes and a surface of the pressed carbon nanotube film is about 0 degrees to approximately 15 degrees. The greater the pressure applied, the smaller the angle obtained.

If the carbon nanotubes in the pressed carbon nanotube film are arranged along different directions, the carbon nanotube structure can be isotropic. Here, "isotropic" means the carbon nanotube film has properties substantially identical in all directions parallel to a surface of the carbon nanotube film. The thickness of the pressed carbon nanotube film ranges from about 0.5 nm to about 1 mm. Examples of pressed carbon nanotube film are taught by US PGPub. 20080299031A1 to Liu et al.

Flocculated Carbon Nanotube Film

In other embodiments, the carbon nanotube film structure 134 includes a flocculated carbon nanotube film. The flocculated carbon nanotube film can include a plurality of long, curved, disordered carbon nanotubes entangled with each other. Further, the flocculated carbon nanotube film can be isotropic. The carbon nanotubes can be substantially uniformly dispersed in the carbon nanotube film. Adjacent carbon nanotubes are acted upon by van der Waals force to obtain an entangled structure with micropores defined therein. It is understood that the flocculated carbon nanotube film is very porous. Sizes of the micropores can be less than 10 µm. The porous nature of the flocculated carbon nanotube film will increase the specific surface area of the carbon nanotube structure.

Furthermore, due to the carbon nanotubes in the carbon nanotube structure being entangled with each other, the carbon nanotube structure employing the flocculated carbon nanotube film has excellent durability, and can be fashioned into desired shapes with a low risk to the integrity of the carbon nanotube structure. The flocculated carbon nanotube film, in some embodiments, will not require the use of a support due to the carbon nanotubes being entangled and adhered together by van der Waals force therebetween. The thickness of the flocculated carbon nanotube film can range from about 0.5 nm to about 1 mm.

Untwisted Carbon Nanotube Wire

Figure 7:
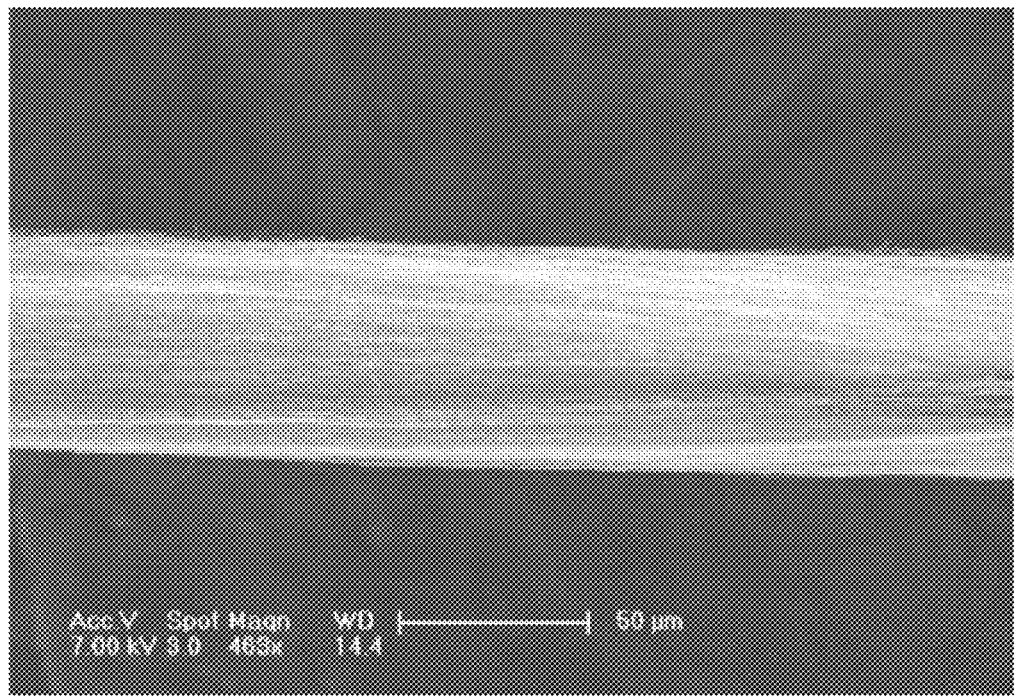
FIG. 7 shows an SEM image of an untwisted carbon nanotube wire.

Treating the drawn carbon nanotube film with a volatile organic solvent can obtain the untwisted carbon nanotube wire. In one embodiment, the organic solvent is applied to soak the entire surface of the drawn carbon nanotube film. During the soaking, adjacent parallel carbon nanotubes in the drawn carbon nanotube film will bundle together, due to the surface tension of the organic solvent as it volatilizes, and thus, the drawn carbon nanotube film will be shrunk into an untwisted carbon nanotube wire. Referring to FIG. 7, the untwisted carbon nanotube wire includes a plurality of carbon nanotubes substantially oriented along a same direction (i.e., a direction along the length direction of the untwisted carbon nanotube wire). The carbon nanotubes are substantially parallel to the axis of the untwisted carbon nanotube wire.

In one embodiment, the untwisted carbon nanotube wire includes a plurality of successive carbon nanotube segments joined end to end by van der Waals force therebetween. Each carbon nanotube segment includes a plurality of carbon nanotubes substantially parallel to each other, and combined by van der Waals force therebetween. The carbon nanotube segments can vary in width, thickness, uniformity, and shape. The length of the untwisted carbon nanotube wire can be arbitrarily set as desired. The diameter of the untwisted carbon nanotube wire ranges from about 0.5 nm to about 100 µm.

Twisted Carbon Nanotube Wire

Figure 8:
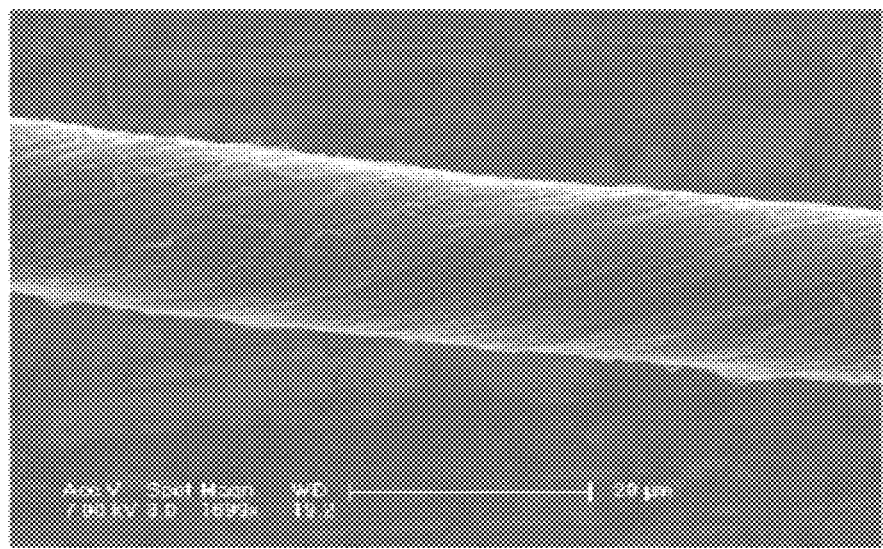
FIG. 8 shows an SEM image of a twisted carbon nanotube wire.

The twisted carbon nanotube wire can be obtained by twisting a drawn carbon nanotube film using a mechanical force to turn the two ends of the drawn carbon nanotube film in opposite directions. Referring to FIG. 8, the twisted carbon nanotube wire includes a plurality of carbon nanotubes helically oriented around an axial direction of the twisted carbon nanotube wire.

In one embodiment, the twisted carbon nanotube wire includes a plurality of successive carbon nanotube segments joined end to end by van der Waals force therebetween. Each carbon nanotube segment includes a plurality of carbon nanotubes substantially parallel to each other, and combined by van der Waals force therebetween. The length of the carbon nanotube wire can be set as desired. The diameter of the twisted carbon nanotube wire can be from about 0.5 nm to about 100 μm.

Furthermore, the twisted carbon nanotube wire can be treated with a volatile organic solvent after being twisted. After being soaked by the organic solvent, the adjacent paralleled carbon nanotubes in the twisted carbon nanotube wire will bundle together due to the surface tension of the organic solvent as the organic solvent volatilizes. The specific surface area of the twisted carbon nanotube wire will decrease, while the density and strength of the twisted carbon nanotube wire will increase.

Figure 9:
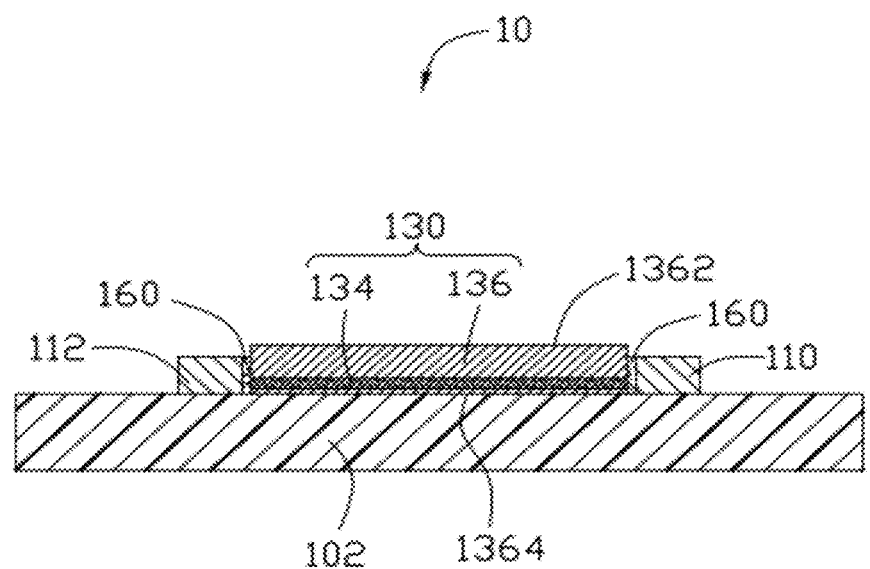
FIG. 9 shows a variation of the thermal therapy device of FIG. 2, in which the heating element is in direct contact with a substrate.

Referring to FIG. 9, the heating element 130 can also be directly disposed on a surface of the substrate 102. Opposite ends of the heating element 130 are attached to and between the first electrode 110 and the second electrode 112 through the conductive adhesive 160 in a one-to-one manner.

Figure 10:
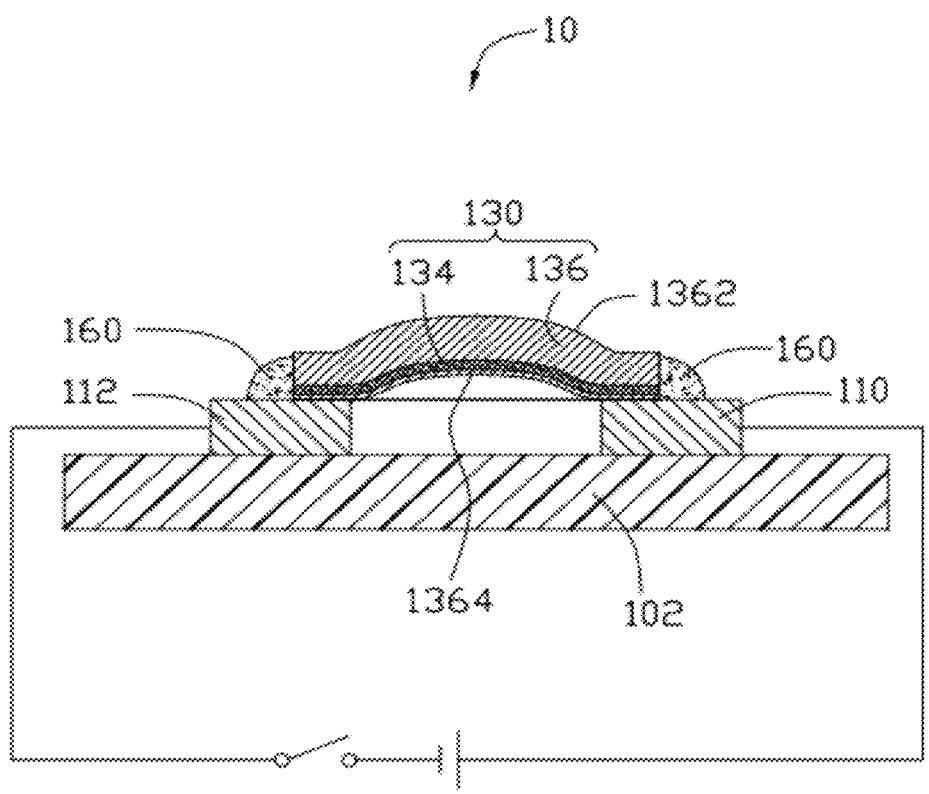
FIG. 10 shows an operational state of the thermal therapy device.

Referring to FIG. 10, the operating principle of the thermal therapy device 10 is shown. When using the thermal therapy device 10, the first surface 1362 of the thermal therapy device 10 is applied on the body and a voltage is applied to the heating element 130 through the first electrode 110 and the second electrode 112. Current flows through the carbon nanotube film structure 134, and the carbon nanotubes convert the electric energy to heat thereby heating the polymer matrix 136. As a result, the temperature of the skin surface and underlying tissues can be increased by the polymer matrix 136. By increasing the temperature of the skin surface and underlying tissues, the heat stimulates the thermoreceptors that respond to hot and cold, which then help block transmissions of pain signals to the brain, thereby increasing comfort.

Furthermore, when the current flows through the carbon nanotube film structure 134, the heat generated by the carbon nanotubes also expands the polymer matrix 136. The thermal expansion coefficients of the polymer matrix 136 and the carbon nanotube film structure 134 are different so that the heating element 130 bends or arches in a direction away from the substrate 102 towards the body, thus generating a massage-like effect in the body. Therefore, the thermal therapy device 10 can generate a massage-like effect in addition to the thermal therapeutic effect, and the thermal therapy device 10 can greatly relieve discomfort.

Moreover, the heating element 130 will resume its original shape after the current cuts off. If the electric current discontinuously flows through the heating element 130, the heating element 130 will periodically rise and fall along the thickness direction of the heating element 130.

In other embodiment, opposite ends of the heating element 130 can also be fixed on the substrate 102 with clips or screws. The first electrode 110 and the second electrode 112 can be spaced apart on the heating element 130. The first electrode 110 and the second electrode 112 can also be put into the polymer matrix 136, so long as the first electrode 110 and the second electrode 112 are electrically connected with the carbon nanotube film structure 134.

Figure 11:
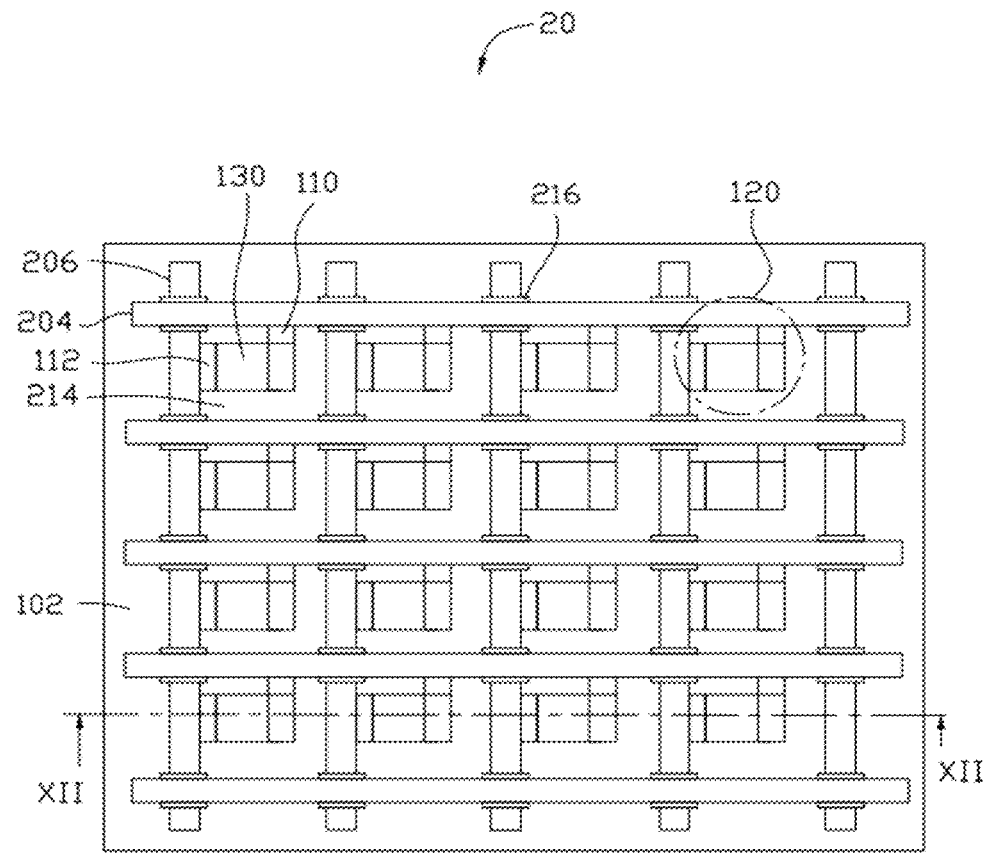
FIG. 11 is a top view of a second embodiment of a thermal therapy device.
Figure 12:
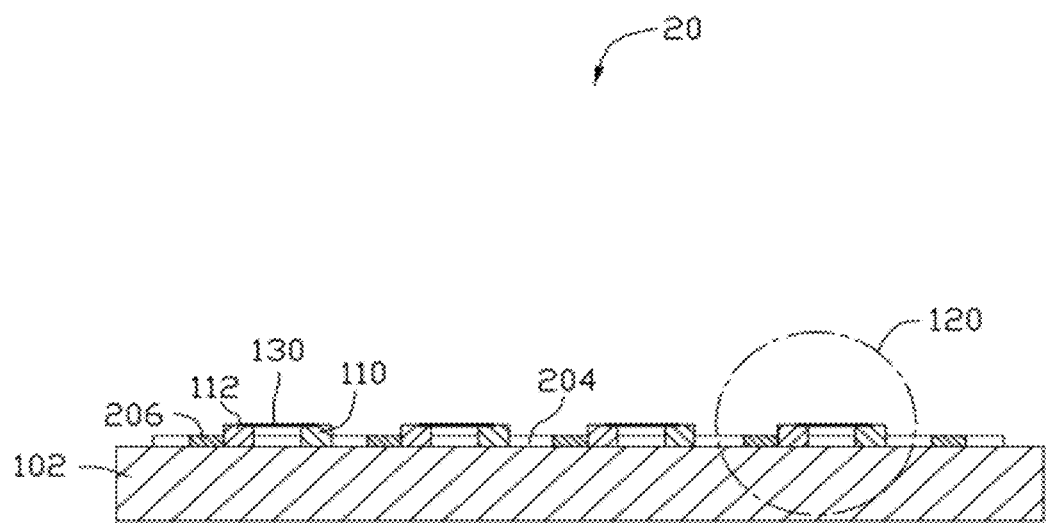
FIG. 12 is a cross-sectional view of the thermal therapy device of FIG. 11, taken along a line XII-XII.

Referring to FIG. 11 and FIG. 12, a second embodiment of a thermal therapy device 20 is shown. The thermal therapy device 20 includes a base 102, a plurality of row electrodes 204, a plurality of column electrodes 206, and a plurality of heating unit 120.

The row electrodes 204 are spaced on the substrate 102. As shown in FIG. 11, the row electrodes 204 each have a strip shape with a lengthwise direction extending from left to right of the thermal therapy device 20. The row electrodes 204 are substantially parallel to each other. The row electrodes 204 can be arranged at non-equal intervals or equal intervals. In one embodiment, the row electrodes 204 can be arranged at an equal interval ranging from about 0.5 centimeters to about 3 centimeters. The row electrodes 204 can have a width ranging from about 300 micrometers to about 5 millimeters, and a thickness ranging from about 0.5 millimeters to about 0.5 centimeters.

The column electrodes 206 are spaced on the substrate 102. The column electrodes 206 each have a strip shape with a lengthwise direction extending from the top to the bottom of the thermal therapy device 20. The column electrodes 206 cross with the row electrodes 204, cooperatively defining a grid having a plurality of openings 214. The column electrodes 206 are insulated from the row electrodes 204 by insulating layers 216 positioned at cross portions of the column electrodes 206 and the row electrodes 204.

The column electrodes 206 can also be arranged at non-equal intervals or equal intervals. In one embodiment, the column electrodes 206 can be arranged at an equal interval ranging from about 0.5 centimeters to about 3 centimeters. The column electrodes 206 can have a width ranging from about 300 micrometers to about 5 millimeters, and a thickness ranging from about 0.5 millimeters to about 0.5 centimeters.

The row electrodes 204 and the column electrodes 206 can be made of metal conductive materials, conductive rubber, or other materials with a conductive layer coated thereon. In one embodiment, the row electrodes 204 and the column electrodes 206 each are a planar conductor made of metal wires which can be attached to a surface of the substrate 102 with adhesive such as polymer binder.

The heating units 120 are arranged on the substrate 102 in the openings 214 in a one-to-one manner. The heating units 120 are arranged along rows and columns to form an array. In each of the openings 214, the first electrode 110 can be electrically connected to the corresponding row electrode 204, and the second electrode 112 can be electrically connected to the corresponding column electrode 206. In other words, the heating units 120, the row electrodes 204, and the column electrodes 206 are arranged on the substrate 102 in such a manner that each of the heating units 120 can be individually controlled to generate heat. Thus, the thermal therapy device 20 can provide better thermal therapeutic effect and massage-like effect.

Figure 13:
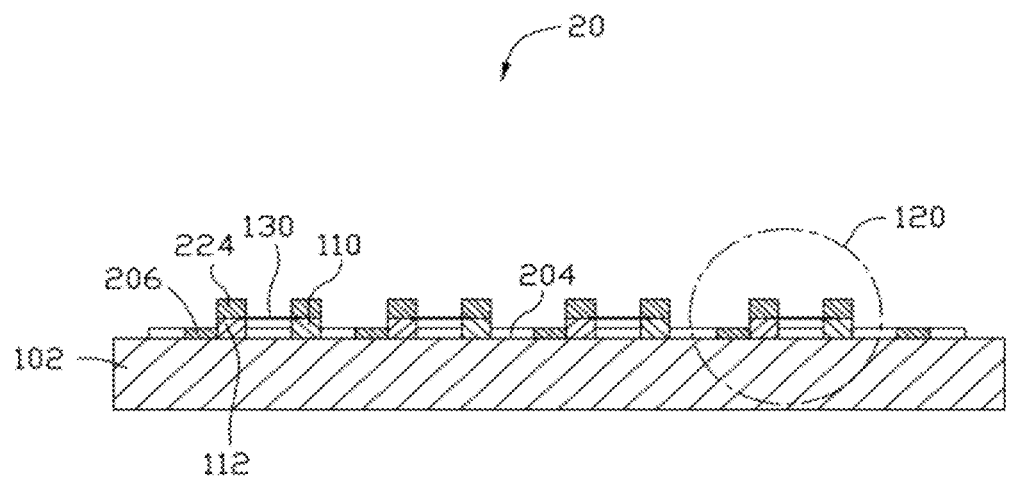
FIG. 13 is similar to FIG. 12 except for the addition of fixing elements.

As shown in FIG. 13, in one embodiment, each of the heating units 120 can further include at least one fixing element 224. The at least one fixing element 224 can be disposed on at least one of the first electrode 110 or the second electrode 112. In the embodiment shown in FIG. 13, each of the heating units 120 includes two fixing elements 224 disposed on the first electrode 110 and the second electrode 112 in a one-to-one manner Opposite ends of the heating element 130 can be clamped between the first electrode 110 and one fixing element 224, and the second electrode 112 and one fixing element 112, respectively. The size and material of the fixing element 224 can be the same as that of the first electrode 110 and the second electrode 112. Furthermore, the thermal therapy device 20 can further include an insulating protective layer coated on the row electrodes 204, the column electrodes 206, the first electrodes 110, and the second electrodes 112, to avoid electric shocks when the thermal therapy device 20 is attached to the body. For example, if the thermal therapy device 20 is positioned at the position shown in FIG. 12, the substrate 102 is horizontally placed, and the row electrodes 204, the column electrodes 206, the first electrodes 110, and the second electrodes 112 are located on a top surface of the substrate 102, then the insulating protective layer can be coated on a top surface of the row electrodes 204, the column electrodes 206, the first electrodes 110, and the second electrodes 112. The insulating protective layer can be made of resin or rubber. In one embodiment, the insulating protective layer can be made of resin, and have a thickness ranging from about 0.5 millimeters to about 2 millimeters. It can be understood that the thermal therapy device 20 can further include a control circuit to control the row electrodes 204 and the column electrodes 206.

Figure 14:
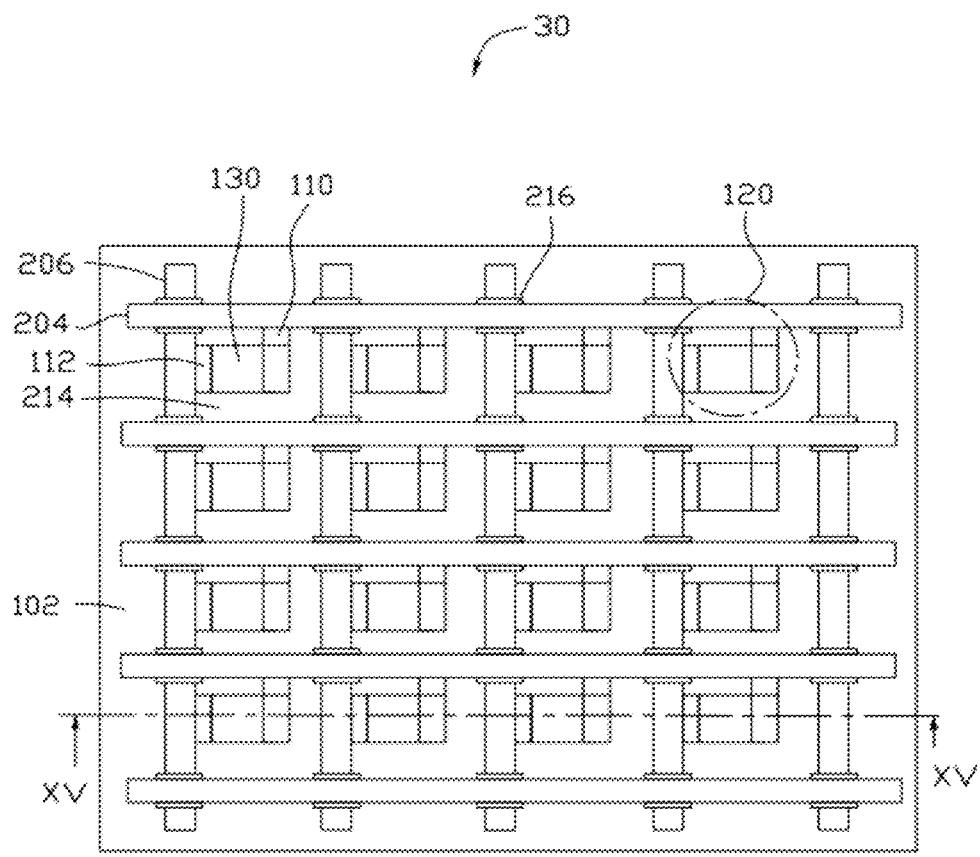
FIG. 14 is a top view of a third embodiment of a thermal therapy device.
Figure 15:
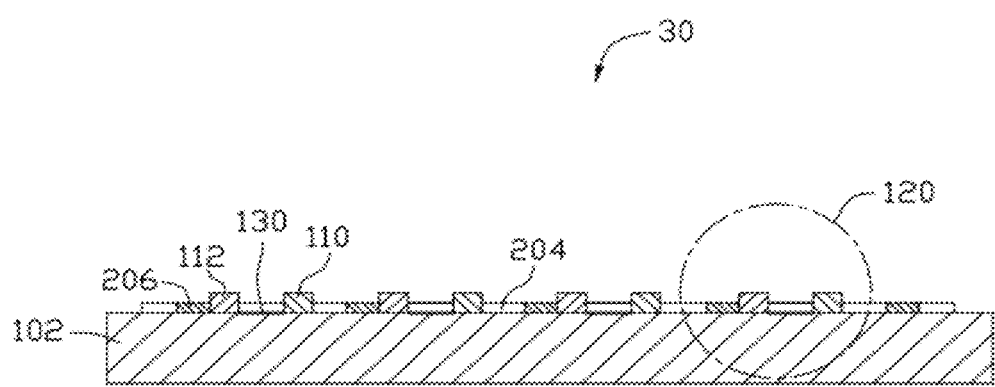
FIG. 15 is a cross-sectional view of the thermal therapy device of FIG. 14, taken along a line XV-XV.

Referring to FIG. 14 and FIG. 15, a third embodiment of a thermal therapy device 30 is shown. The third embodiment is similar to the second embodiment, except that the heating elements 130 are directly formed on the substrate 102 in a same manner as that shown in FIG. 9. As shown in FIG. 15, the substrate 102 is horizontally placed, and the row electrodes 204, the column electrodes 206, the first electrodes 110, and the second electrodes 112 are located on a top surface of the substrate 102, the heating elements 130 are directly disposed on the top surface of the substrate 102. Opposite ends of each of the heating elements 130 are attached to and between the corresponding first electrode 110 and the second electrode 112 in a one-to-one manner.

It is to be understood that the above-described embodiments are intended to illustrate rather than limit the disclosure. Variations may be made to the embodiments without departing from the spirit of the disclosure as claimed. It is understood that any element of any one embodiment is considered to be disclosed to be incorporated with any other embodiment. The above-described embodiments illustrate the scope of the disclosure but do not restrict the scope of the disclosure.

Depending on the embodiment, certain of the steps of methods described may be removed, others may be added, and the sequence of steps may be altered. It is also to be understood that the description and the claims drawn to a method may include some indication in reference to certain steps. However, the indication used is only to be viewed for identification purposes and not as a suggestion as to an order for the steps.

What is claimed is:

1. A thermal therapy device comprising: a substrate;
a plurality of row electrodes supported by the substrate;
a plurality of column electrodes supported by the substrate and insulated from the row electrodes; and
a plurality of heating units located on the substrate, wherein each of the heating units comprises a first electrode, a second electrode, and a heating element electrically connected to the first electrode and the second electrode;
wherein the heating element comprises a carbon nanotube film structure and a polymer matrix, the carbon nanotube film structure is substantially parallel to and offset from a central plane of the polymer matrix, and the polymer matrix has a surface adjacent to the substrate, the carbon nanotube film structure is disposed in the polymer matrix and is adjacent to the surface of the polymer matrix, the row electrodes are crossed with the column electrodes, cooperatively forming a grid defining a plurality of openings, the heating units are arranged in the openings in a one-to-one manner, and in each of the openings, the first electrode and the second electrode are electrically connected to one of the row electrodes and one of the column electrodes, respectively; wherein thermal expansion coefficients of the polymer matrix and the carbon nanotube film structure are different so that the heating element is configured to bend in a direction away from the substrate when current flows through the carbon nanotube film structure.

2. The thermal therapy device of claim 1, wherein in each of the heating units, one end of the heating element is installed on the first electrode, and an opposite end of the heating element is installed on the second electrode.

3. The thermal therapy device of claim 2, wherein the first electrode and the second electrode separate the heating element from the substrate.

4. The thermal therapy device of claim 2, wherein the heating element is directly disposed on the substrate between the first electrode and the second electrode.

5. The thermal therapy device of claim 1, wherein each of the heating units further comprises at least one fixing element disposed on at least one of the first electrode and the second electrode, and at least one end of the heating element is clamped between the at least one fixing element and one of the first electrode and the second electrode.

6. The thermal therapy device of claim 1, further comprising an insulating protective layer coated on the row electrodes, the column electrodes, the first electrodes, and the second electrodes.

7. The thermal therapy device of claim 1, wherein the carbon nanotube film structure is a drawn carbon nanotube film, a flocculated carbon nanotube film, a pressed carbon nanotube film, or combinations thereof.

8. The thermal therapy device of claim 1, wherein the carbon nanotube film structure is an untwisted carbon nanotube wire, a twisted carbon nanotube wire, or combinations thereof.

9. The thermal therapy device of claim 1, wherein the central plane is parallel with the substrate, the polymer matrix is divided into a first portion and a second portion via the central plane, and the carbon nanotube film structure is accommodated in the first portion.

10. A thermal therapy device comprising:
a substrate;
a plurality of row electrodes;
a plurality of column electrodes; and
a plurality of heating units arranged along rows and columns on the substrate;
wherein each of the heating units comprises a heating element electrically connected to one of the row electrodes and one of the column electrode, and the heating unit is a planar thin film structure, the heating element comprises a carbon nanotube film structure and a polymer matrix, the carbon nanotube film structure is offset from a central plane of the polymer matrix through a thickness of the polymer matrix, and the polymer matrix has a surface adjacent to the substrate, the carbon nanotube film structure is accommodated in the polymer matrix and is adjacent to the surface of the polymer matrix, and the row electrodes and the column electrodes are arranged on the substrate in such a manner that each of the heating units is individually controlled to generate heat; wherein thermal expansion coefficients of the polymer matrix and the carbon nanotube film structure are different so that the heating element is configured to bend in a direction away from the substrate when current flows through the carbon nanotube film structure.

11. The thermal therapy device of claim 10, wherein the carbon nanotube film structure is substantially parallel to the central plane of the polymer matrix.

12. The thermal therapy device of claim 10, wherein each of the heating units further comprises a first electrode and a second electrode, one end of the heating element is installed on the first electrode, and an opposite end of the heating element is installed on the second electrode.

13. The thermal therapy device of claim 12, wherein the first electrode and the second electrode separate the heating element from the substrate.

14. The thermal therapy device of claim 12, wherein the heating element is directly disposed on the substrate between the first electrode and the second electrode.

15. The thermal therapy device of claim 12, further comprising an insulating protective layer coated on the row electrodes, the column electrodes, the first electrodes, and the second electrodes.

16. A thermal therapy device comprising a substrate and at least one heating unit arranged on the substrate, wherein the at least one heating unit comprises a heating element, a first electrode, and a second electrode, the heating element comprises a carbon nanotube film structure and a polymer matrix, the carbon nanotube film structure is substantially parallel to and offset from a central plane of the polymer matrix, and the first electrode and the second electrode are electrically connected to the carbon nanotube film structure, and control the amount of heat and deformation produced by the carbon nanotube film structure; wherein thermal expansion coefficients of the polymer matrix and the carbon nanotube film structure are different so that the heating element is configured to bend in a direction away from the substrate when current flows through the carbon nanotube film structure.

17. The thermal therapy device of claim 16, wherein the first electrode and the second electrode separate the heating element from the substrate.

18. The thermal therapy device of claim 16, wherein the heating element is directly disposed on the substrate between the first electrode and the second electrode.

19. The thermal therapy device of claim 16, further comprising an insulating protective layer coated on the first electrode and the second electrode.

20. The thermal therapy device of claim 16, wherein the at least one heating unit further comprises two fixing elements disposed on the first electrode and the second electrode in a one-to-one manner, opposite ends of the heating element are clamped between the first electrode and one of the two fixing elements, and the second electrode and the other one of the two fixing elements, respectively.

* * * * *